(12) United States Patent
Linders et al.

(10) Patent No.: US 6,292,534 B1
(45) Date of Patent: Sep. 18, 2001

(54) X-RAY EXAMINATION APPARATUS

(75) Inventors: Petrus W. J. Linders; Hendrik J. Meulenbrugge, both of Eindhoven (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/208,505

(22) Filed: Dec. 9, 1998

(30) Foreign Application Priority Data

Dec. 10, 1997 (EP) .................................................. 97203873

(51) Int. Cl.$^7$ ....................................................... G01T 1/00
(52) U.S. Cl. ........................ 378/98.2; 378/98.8; 378/205
(58) Field of Search ................................. 378/98.2, 98.4, 378/98.7, 98.8, 95, 189, 205, 207, 209

(56) References Cited

U.S. PATENT DOCUMENTS

| 4,669,105 |   | 5/1987  | Fenster et al.  | 378/145  |
|-----------|---|---------|-----------------|----------|
| 5,530,935 | * | 6/1996  | Dillen          | 378/98.2 |
| 5,574,764 | * | 11/1996 | Granfors et al. | 378/98.7 |
| 5,883,937 | * | 3/1999  | Schmitt         | 378/189  |

* cited by examiner

*Primary Examiner*—David P. Porta
(74) *Attorney, Agent, or Firm*—John F. Vodopia

(57) ABSTRACT

An X-ray examination apparatus includes an X-ray detector for deriving an image signal from an X-ray image. The X-ray detector has an essentially elongate X-ray-sensitive surface. The X-ray sensitive surface of the X-ray detector corresponds notably to a relevant part of the object to be examined.

13 Claims, 3 Drawing Sheets

X-RAY EXAMINATION APPARATUS

BACKGROUND OF THE INVENTION

The invention relates to an X-ray examination apparatus.

An X-ray examination apparatus of this kind is known from European patent Application 08/926 867.

The known X-ray examination apparatus is used to pick up successive X-ray images by means of an image intensifier pick-up chain which includes an X-ray image intensifier and a television camera. The X-ray image intensifier includes an entrance screen provided with an X-ray sensitive conversion layer. The X-ray image intensifier has a substantially circular X-ray sensitive surface. Consequently, it is not very well possible to make the X-ray sensitive surface so large that a substantial part of the patient to be examined, for example the limbs, can be imaged in a single X-ray image. In the known Xray examination apparatus separate parts of an object, for example a patient to be radiologically examined, are irradiated by means of an X-ray beam and a series of successive X-ray images of the relevant parts of the patient is formed on the entrance screen of the Xray image intensifier; these X-ray images are converted into successive optical images on the exit window of the X-ray image intensifier and the television camera derives electronic video signals from the successive optical images. An image processing unit forms an image signal which represents the assembled image from the electronic video signals. The assembled image shows the separate parts of the patient together in a single image.

SUMMARY OF THE INVENTION

It is an object of the invention to provide an X-ray examination apparatus which enables an X-ray image to be formed of a substantial part of an object to be examined while utilizing a lower X-ray dose in comparison with the known X-ray examination apparatus.

This object is achieved by means of an X-ray examination apparatus according to the invention which is characterized in that the X-ray detector has an essentially elongate X-ray sensitive surface, or the read-out circuit is arranged to read-out a selected part of the X-ray detector. Preferably, the X-ray detector or the selected part that is read-out has a width to length ratio less that ⅝ or even less than ½ or ⅔. Such values of the width to length ratio appear to correspond accurately to the shape of a patent's leg so that the X-ray detector according to the invention is advantageously employed in peripheral angiographic X-ray examinations.

The X-ray examination apparatus includes an X-ray source for irradiating an object, for example a patient to be examined, by means of an X-ray beam. An X-ray image is formed on the X-ray sensitive surface due to local differences in the X-ray absorption within the patient. Such an elongate X-ray detector enables an X-ray image to be made of a substantial part of the patient to be examined, without it being necessary to displace the X-ray source and the X-ray detector together and relative to the patient so as to form individual sub-images. Because only a single X-ray exposure is required, the X-ray dose required is much lower than in the known X-ray examination apparatus. Moreover, the construction of the X-ray examination apparatus according to the invention is less complex than that of the known X-ray examination apparatus. It is notably no longer necessary to perform a complex image processing operation so as to merge sub-images into a high-quality diagnostic image in which substantially the entire region to be examined is reproduced in such a manner that small details of low contrast are still suitably visible; for example, substantially the entire vascular system of a leg of the patient is reproduced in the X-ray image.

It has been found in practice that in many radiological examinations the relevant part of the X-ray image used has an essentially elongate shape. Consequently, the X-ray examination apparatus according to the invention offers the advantage that the shape of the X-ray sensitive surface corresponds better to the relevant part of the X-ray image than in a conventional X-ray examination apparatus. An X-ray image of a part of the patient to be examined can thus be formed by means of a single X-ray exposure while utilizing essentially the entire X-ray detector nevertheless. The surface of the X-ray detector need not be much larger than the surface of the part of the patient to be examined.

It is also possible to realize an X-ray detector having a desired X-ray sensitive surface by combination of individual X-ray detector modules. Such X-ray detector modules are preferably manufactured so as to have standard dimensions.

An X-ray detector having a substantially elongate X-ray sensitive surface is, for example an image sensor matrix. Such an image sensor matrix includes, for example X-ray-sensitive sensor elements which are arranged in a matrix. Individual sensor elements are connected to a read-out line by means of a switching element. Individual switching elements are connected to a control line. Incident X-rays are converted into electric charges in the sensor elements. The sensor elements are made of, for example a material which converts X-rays into electric charges, for example amorphous hydrated silicon ($\alpha$-Si:H) or an X-ray sensitive photoconductor such as selenium (Se) or lead oxide (PbO). An X-ray detector of this kind is known from European patent applications EP 0 444 720 and EP 0 440 282. The sensor elements can alternatively be constructed as infrared-sensitive, ultraviolet-sensitive or photosensitive elements, such as photodiodes or phototransistors; the image sensor matrix is then also provided with a conversion layer for converting incident X-rays into radiation whereto the sensor elements are sensitive.

The X-ray detector having a substantially elongate surface may also be an X-ray detector which is provided with an essentially flat conversion screen for deriving optical images from the X-ray images, and with an image pick-up system with one or more image sensors for deriving image signals from the optical images.

The conversion screen is provided with an essentially flat layer of scintillation material, such as doped cesium iodide (CsI). The X-ray images are formed substantially without distortion on the conversion screen. The conversion screen converts an X-ray image into a radiation image of infrared or ultraviolet radiation or visible light. Sub-image signals are derived from individual radiation images by means of one or more image sensors. The image processing unit processes such sub-image signals so as to form an image signal for the assembled image. The image processing unit can operate with a fixed setting because the image sensors occupy a known position relative to the conversion screen and the settings of the individual image sensors, such as an internal amplification, do not change during the picking up of the image. An X-ray detector of this kind is known per se from European patent application EP 0 583 844.

These and other aspects of the invention will be described on the basis of the embodiments defined in the dependent Claims.

When the X-ray detector is integrated in the patient table, it is achieved that the X-ray examination apparatus according to the invention occupies less space than the known apparatus. The X-ray detector accommodated in the patient table is also suitably protected, so that it cannot be easily damaged. Furthermore, it is not necessary to clean or sterilize the X-ray detector when it is accommodated in the patient table. Moreover, the X-ray detector can be suspended independently of the X-ray source, so that there are hardly any restrictions as regards the accessibility of the examination space in which the patient is arranged during the formation of the X-ray images. Notably when the X-ray detector extends over a large part of the length of the patient table and the X-ray source is movable independently of the X-ray detector, digital tomosynthesis can be performed during which the X-ray detector forms an image of a longitudinal cross-section of the patient to be examined. Such a tomosynthesis technique is known per se from the book "Bildgebende Systeme für die medizinische Diagnostik" by Erich Krestel (2nd edition 1988), notably from the chapter "Tomosynthese" (7.2.6). The X-ray source is preferably connected to its own suspension so that it can be displaced separately relative to the patient table. Such a suspension of the X-ray source is preferably connected to the ceiling of the examination room in which the X-ray examination apparatus is installed. The X-ray source can thus be moved over the patient table, during which movement the access to the examination space in which the patient is arranged during the formation of the X-ray images is not or only hardly impeded by the suspension of the X-ray source.

The patient table surface supporting the patient is situated between the X-ray detector and the X-ray source. During operation the X-ray detector is situated at some distance from the patient to be examined, because the patient and the X-ray detector are arranged to both sides of the surface of the patient table supporting the patient. The distance between the X-ray detector and the patient ensures that disturbing effects of scattered rays on the X-ray image are reduced. The disturbing effect of scattered X-rays is substantially reduced when the distance between the patient and the X-ray detector is in the range 5–30 cm. Very good results are achieved when the distance between the patient and the X-ray detector is in the range 10–15 cm. Often, when the X-ray detector is incorporated in the patient table the distance between the X-ray detector and the patient is sufficient to reduce disturbances in the X-ray image due to scattered X-rays. The disturbing effect of the scattered X-rays is reduced by this distance because a substantial amount of scattered X-rays passes by the X-ray detector and as the distance between the X-ray detector and the patient is larger, the spatial variations of the scattered X-ray intensity is less. The distance between the X-ray detector and the patient should not be made too large so as to avoid blurring of the image due to the fact that the X-ray source has a finite size and is not a point-source. This reduction is so extensive that an anti-scatter grid is no longer required or that, if necessary, use can be made of an anti-scatter grid satisfying very broad tolerances. If no anti-scatter grid is used, the X-ray dose required to form an X-ray image of high diagnostic quality is less than when use is made of an anti-scatter grid. Moreover, if no anti-scatter grid is used, it cannot introduce disturbances in the X-ray image.

The X-ray source and the X-ray detector are preferably movable independently of one another. The X-ray detector comprises individual detection elements. For example, in case the X-ray detector is an image sensor matrix, the sensor elements constitute the detection elements or the photosensitive elements of the image pick-up apparatus act as the detection elements. As the part of the X-ray detector which is selected to be read out is smaller, less time will be required for reading out. Therefore, when it is not necessary to read out all detection elements, the time required to derive an image signal from the X-ray image by means of the X-ray detector can be reduced. Such a situation occurs when the detection elements do not all contain image information or if image information is relevant in only a part of the detection elements.

The X-ray examination apparatus preferably includes a collimator for spatially limiting an X-ray beam, the X-ray detector being provided with a read-out circuit which is arranged to read out a part of the X-ray detector which is reached by the limited X-ray beam. The collimator ensures that essentially only a part of the patient to be examined which is to be imaged is exposed to X-rays. To this end, the collimator includes collimator elements which can hardly be penetrated by X-rays and which can be arranged in the X-ray beam so as to form a limited X-ray beam having the desired cross-section. The collimator elements intercept a part of the X-rays so that the X-ray beam transmitted by the collimator is limited in space. Consequently, an X-ray image is formed only on the part of the X-ray detector that can be reached by the X-rays. When only this relevant part is read out, no time will be wasted on the unnecessary reading out of parts of the X-ray detector in which no X-ray image has been formed. The technical measure of reading-out a selected part of the Xray detector is also advantageously used independently of the shape of the X-ray detector. Notably, also X-ray detectors which have an X-ray sensitive surface that is not elongate are preferably read-out only with respect to portions of the X-ray detector that contain useful image information.

The dimensions of the X-ray-sensitive surface of the X-ray detector preferably correspond essentially to a part of an object to be radiologically imaged. The part to be radiologically imaged is reproduced in the X-ray image by the X-rays. The X-ray image of the part of the object to be examined, for example the vascular system in the legs of the patient, fits accurately on the X-ray-sensitive surface of the X-ray detector. It is thus achieved that the desired image is formed on the X-ray detector in a single step so that it is not necessary to merge separate sub-images. Because the desired image is formed in a single step, disturbances in the image which are caused by the merging of sub-images are avoided. Furthermore, essentially the complete X-ray detector is effectively used; there are hardly parts of the X-ray detector which are not used to form the X-ray image.

BRIEF DESCRIPTION OF THE DRAWINGS

These and other aspects of the invention will be explained in detail on the basis of the following embodiments and with reference to the accompanying drawing; therein.

DESCRIPTION OF THE PREFEERED EMBODIMENTS

Figure 1:
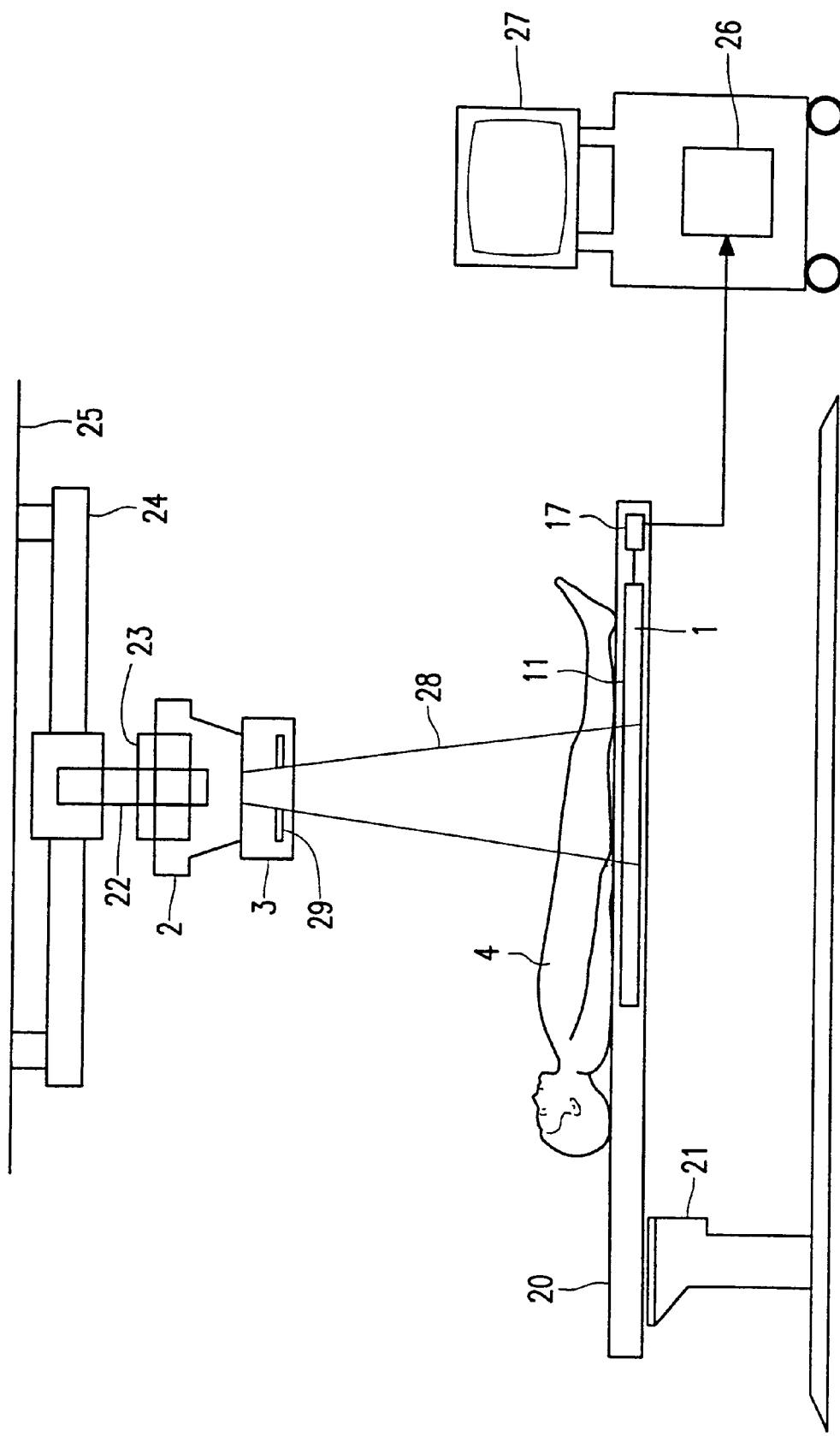
FIG. 1 is a diagrammatic side elevation of an X-ray examination apparatus in which the invention is used.

FIG. 1 shows diagrammatically an X-ray examination apparatus in which the invention is used. The X-ray examination apparatus includes an X-ray detector 1 which is integrated in the patient table 20. The X-ray examination apparatus also includes an X-ray source 2 which is adjustably connected to a support 22 by means of a suspension 23. The patient table 20 is mounted on a height-adjustable pillar 21. The height of the X-ray source relative to the patient 4 can be adjusted by adjustment of the position of the X-ray source 2 on the support 22 and/or of the height of the pillar 21. The suspension 23 enables displacement of the X-ray source 2 in the direction transversely of the longitudinal direction of the patient. The support 22 is suspended from rails which are mounted on the ceiling 25 of the examination room in which the X-ray examination apparatus is installed. The support 22 is displaceable on the rails 24 in the longitudinal direction of the patient table.

The patient 4 is irradiated by means of an X-ray beam 28 from the X-ray source 2 in order to form an X-ray image of a part of the patient. The X-ray source 2 includes a collimator with lead collimator elements 29 for spatially limiting the X-ray beam. The collimator elements 29 are displaceable transversely of the (central ray of the) X-ray beam. An X-ray image is formed on the X-ray sensitive surface 11 of the X-ray detector due to local differences in the X-ray absorption within the patient. The X-ray detector 1 is an electronic digital X-ray detector. The X-ray detector 1 converts incident X-rays into electric charges which correspond to the brightness values of the X-ray image. The X-ray detector 1 includes a read-out circuit 17 which applies an image signal, for example an electronic video signal, to an image processing unit 26. The image processing unit 26 is arranged to correct the image signal at least partly for known error sources and disturbances. The processed image signal formed by the image processing unit 26 is applied to a monitor 27 in order to display the image information contained in the X-ray image.

Figure 2:
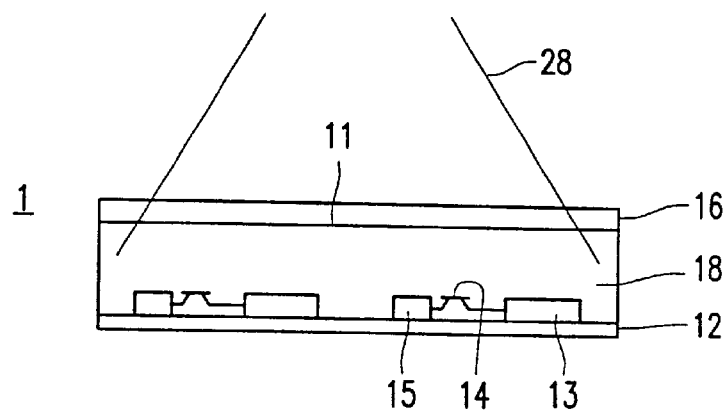
FIG. 2 shows diagrammatically embodiments of an X-ray detector of an X-ray examination apparatus according to the invention.

FIG. 2 shows diagrammatically an embodiment of an X-ray detector 1, in the form of a cross-sectional view of an image sensor matrix, of an X-ray examination apparatus according to the invention. An electrode structure is provided on a glass substrate 12 by means of a thin-film technique. This structure includes collector electrodes 13 which are coupled to read-out lines 15 by way of thin-film transistors 14. The gate electrodes of the thin-film transistors are connected to addressing lines 19 which are not visible in the cross-sectional view. The present example shows only two collector electrodes, but in practice an image sensor matrix includes a large number of, for example 400 read-out lines and 600 addressing lines and 400×600 collector electrodes with thin-film transistors. The electrode structure is covered with an X-ray-sensitive layer 18 of a photoconductive material such as selenium (Se) or lead oxide (PbO). At the side of the X-ray sensitive layer which is remote from the electrode structure there is provided a common counter electrode 16. An electric voltage is applied across the X-ray sensitive layer 18 during operation. Incident X-rays generate charge carriers in the X-ray sensitive layer, which carriers are collected in the collector electrodes and subsequently read out via the read-out lines. The X-ray-sensitive layer 18 is flat and notably has a flat surface 11 on which the X-rays are incident. Consequently, hardly any geometrical distortions occur in the X-ray image. Reading out is controlled by switching the thin-film transistors 14 by means of signals conducted by the addressing lines 19. The read-out unit 17 converts the charges read out, representing brightness values of the X-ray image, into the image signal. An image sensor matrix of this kind is known per se from European patent applications EP 0 444 720 and EP 0 440 282.

Figure 3:
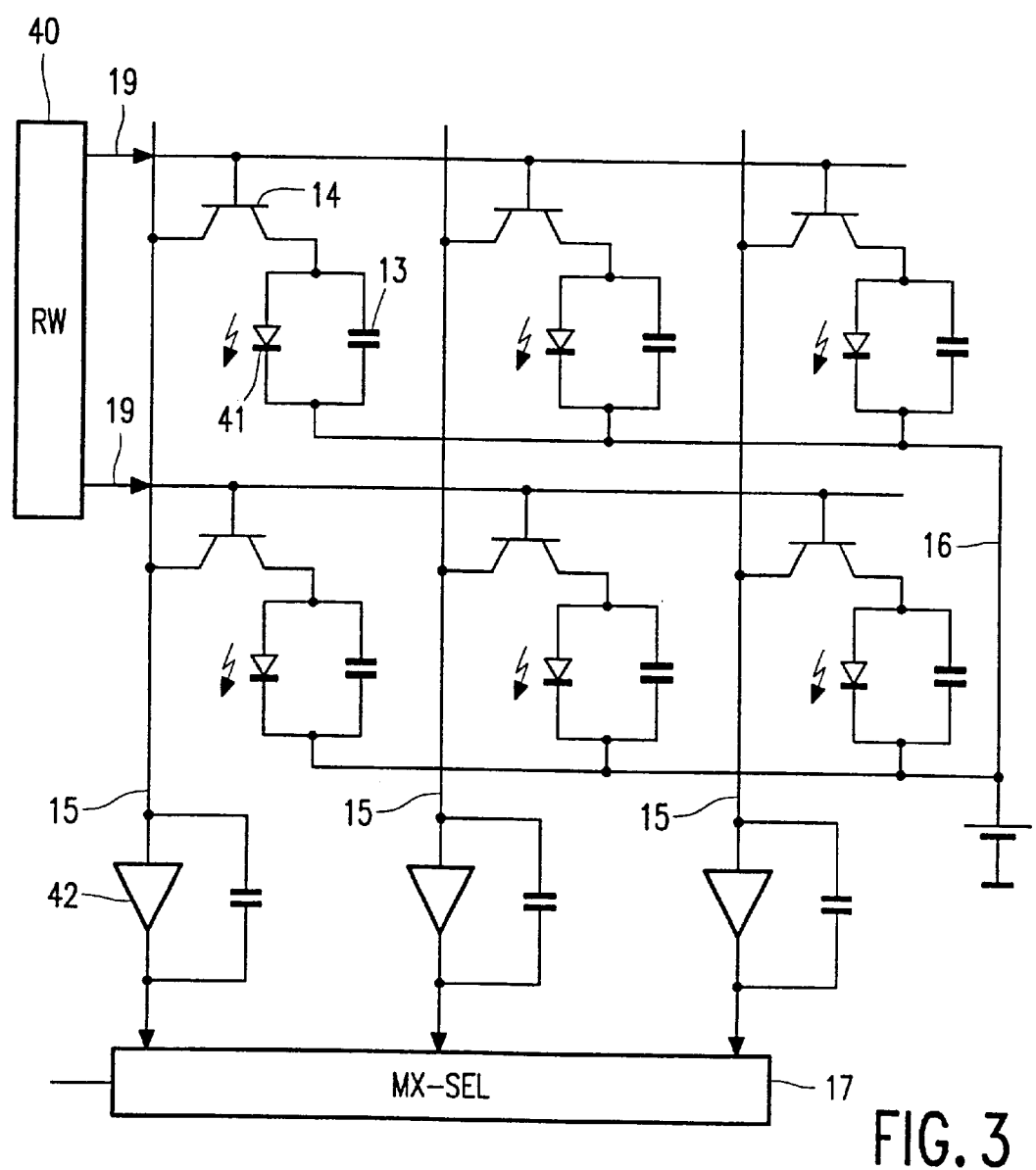
FIG. 3 shows a diagram of an electronic circuit of the X-ray detector of FIG. 2.

FIG. 3 shows a diagram of an electronic circuit of the X-ray detector of FIG. 2. For the sake of simplicity, FIG. 3 shows an image sensor matrix comprising only 2×3 sensor elements. In practice, however, use is made of an image sensor matrix comprising 400×600 or even more sensor elements. Each of the sensor elements is provided with a photodiode 41 which is connected parallel to a capacitance. In practice this capacitance is formed by the self-capacitance of the photodiode 41. The capacitances are formed each time by the relevant collector electrode 13 and the counter electrode 16. Per column the collector electrodes 13 are connected to the read-out lines 15 via the thin-film MOS transistors 14. Per row each of the thin-film transistors is connected, by way of its gate contact, to the addressing lines 19. The thin-film transistors 14 are switched per row by a row driver 40. The electric charges read from the capacitances are applied column by column to integrating read-out amplifiers 42. The integrating read-out amplifiers convert the charges of the individual columns into electric voltages which are applied to a multiplexer selector circuit 17. The multiplexer selector circuit selects parts, notably columns, of the image sensor matrix which are read out. The multiplexer selector circuit activates the integrating read-out amplifiers of the columns which are read out. The multiplexer selector circuit also acts as a read-out circuit for deriving the electronic video signal, representing the X-ray image, from the electric voltages from the integrating read-out amplifiers.

Figure 4:
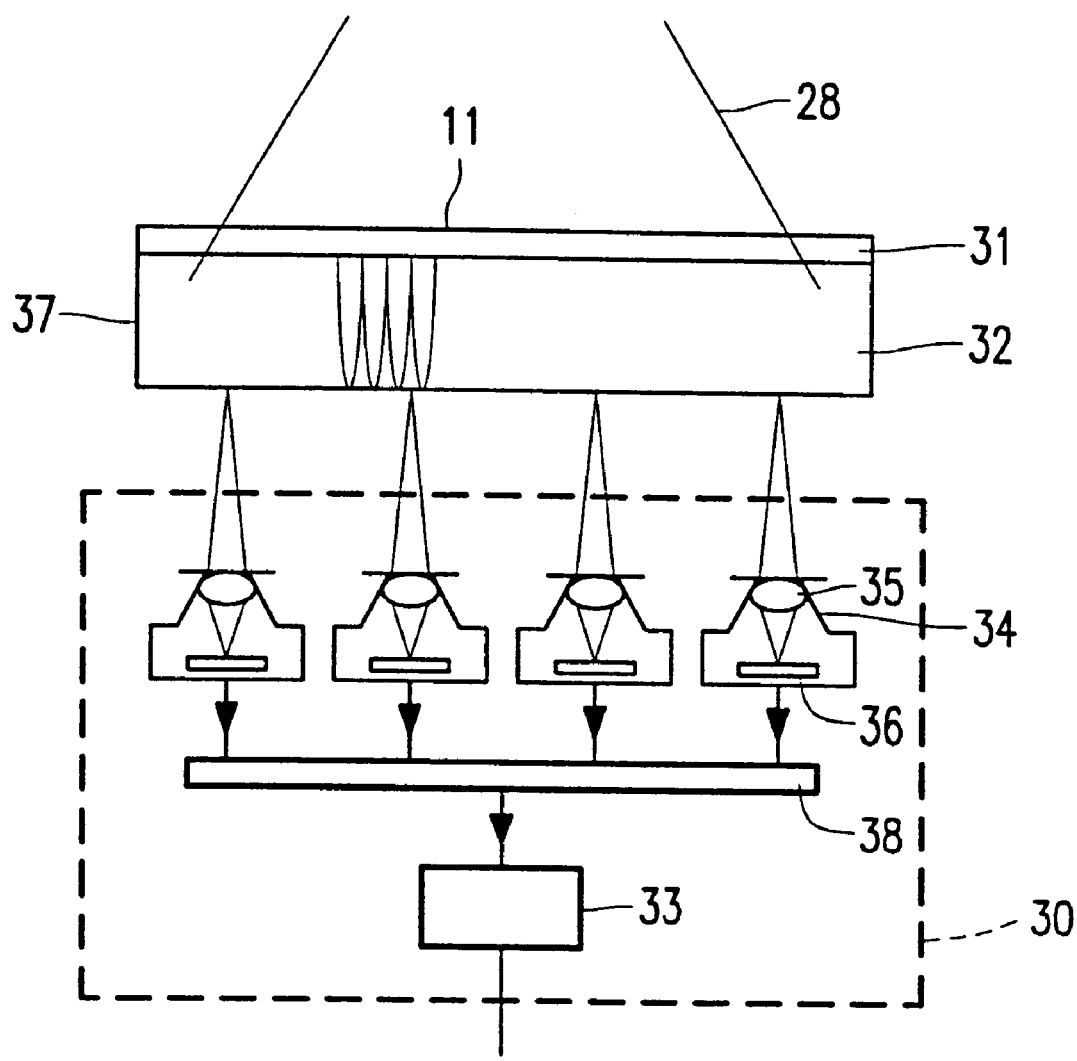
FIG. 4 shows diagrammatically a further embodiment of an X-ray detector 1 of an X-ray examination apparatus according to the invention.

FIG. 4 shows diagrammatically a further embodiment of an X-ray detector 1 of an X-ray examination apparatus according to the invention. The X-ray detector of FIG. 2 includes a conversion screen 37 which includes a scintillation layer 32 provided on a substrate 31. The substrate 31 is, for example a thin aluminium foil which suitably transmits X-rays and the scintillation layer 32 is, for example a cesium iodide layer doped with thallium or sodium(CsI:T, CsI:Na)). The scintillation layer converts incident X-rays into low-energetic radiation, for example red or green light. The scintillation layer has a flat surface 11 on which the X-rays 28 are incident; consequently, hardly any geometrical distortions occur in the X-ray image. The low-energetic radiation, i.e. the green or red light, emanates from the conversion screen 37 at the side of the conversion screen 37 which is remote from the X-ray source. The conversion screen 37 thus converts the X-ray image into an optical image. The scintillation layer 32 preferably contains column-shaped cesium iodide crystals which extend approximately transversely to the scintillation layer. Such crystals act as photoconductive channels which conduct the low-energetic radiation substantially perpendicularly to the scintillation layer so that the low-energetic radiation is hardly dispersed in the plane of the scintillation layer. This results in a high spatial resolution of the X-ray detector 1. The X-ray detector 1 also includes an image pick-up system 30 with a plurality of image pick-up apparatus 34, such as television cameras. Each television camera includes a camera lens 35 and an image sensor 36. Each camera lens 35 images a part of the optical image on the conversion screen 37 onto the relevant image sensor 36. Such an image sensor is, for example a charge coupled (CCD) semiconductor sensor. The individual television cameras supply sub-image signals which represent brightness values of a part of the optical image of the conversion screen. The sub-image signals are applied to a combination unit 33 via a bus 38. The combination unit derives an image signal which represents the optical image of the conversion screen from the sub-image signals. Generally speaking, the conversion screen converts the X-ray image into an optical image and the image pick-up system derives the image signal from the optical image. An X-ray detector of this kind is known per se from European patent application EP 0 583 844.

All references cited herein are incorporated herein by reference in their entirety and for all purposes to the same extent as if each individual publication or patent or patent application was specifically and individually indicated to be incorporated by reference in its entirety for all purposes.

What is claimed is:

1. An X-ray examination apparatus comprising:
   an X-ray collimator for spatially limiting an X-ray beam, and
   an X-ray detector for receiving the spatially limited X-ray beam and deriving an image signal from an X-ray image formed thereby, the X-ray detector including a read-out circuit wherein the read-out circuit is arranged to readout only a selected part of the X-ray detector at which said spatially limited x-ray beam is capable of reaching.

2. An X-ray examination apparatus as claimed in claim 1 wherein the selected part of the X-ray detector has a width to length ratio less than 5/8.

3. The apparatus of claim 2 wherein the width to length ratio less than ½.

4. An X-ray examination apparatus as claimed in claim 1 wherein the part which is read-out corresponds essentially to a part of an object to be radiologically imaged.

5. The apparatus of claim 2 wherein the width to length ratio less than 2/5.

6. An X-ray examination apparatus as claimed in claim 1 further comprising an object carrier for carrying an object to be examined, the X-ray detector and the object carrier being spaced apart by a separation distance which substantially reduces disturbing effects of scattered X-rays on the X-ray image.

7. An X-ray examination apparatus comprising an X-ray collimator for spatially limiting an X-ray beam, and an X-ray detector for receiving the spatially limited X-ray beam and deriving an image signal from an X-ray image derived from only the portion of the x-ray detector at which said spatially limited X-ray beam is capable of reaching, wherein the X-ray detector has an essentially elongate shape with a width to length ratio of approximately less than 5/8.

8. An X-ray examination apparatus as claimed in claim 7, further comprising a patient table, and wherein the X-ray detector is accommodated in or mounted under the patient table.

9. The apparatus of claim 7 wherein the width to length ratio less than ½.

10. The apparatus of claim 9 further comprising an object carrier for carrying an object to be examined, the X-ray detector and the object carrier being spaced apart by a separation distance which substantially reduces disturbing effects of scattered X-rays on the X-ray image.

11. The apparatus of claim 7 wherein the width to length ratio less than 2/5.

12. The apparatus of claim 7 further comprising an object carrier for carrying an object to be examined, the X-ray detector and the object carrier being spaced apart by a separation distance which substantially reduces disturbing effects of scattered X-rays on the X-ray image.

13. The apparatus of claim 11 further comprising an object carrier for carrying an object to be examined, the X-ray detector and the object carrier being spaced apart by a separation distance which substantially reduces disturbing effects of scattered X-rays on the X-ray image.

* * * * *